(12) United States Patent
Zhao et al.

(10) Patent No.: US 8,030,015 B2
(45) Date of Patent: Oct. 4, 2011

(54) TUMOR-INHIBITING PROTEIN AND THE USE THEREOF

(75) Inventors: Mujun Zhao, Shanghai (CN); Zhenhua Xu, Shanghai (CN); Liang Liang, Shanghai (CN); Zaiping Li, Shanghai (CN)

(73) Assignee: Shanghai Institutes for Biological Sciences, Chinese Academy of Sciences, Shanghai (CN)

( * ) Notice: Subject to any disclaimer, the term of this patent is extended or adjusted under 35 U.S.C. 154(b) by 313 days.

(21) Appl. No.: 12/171,112

(22) Filed: Jul. 10, 2008

(65) Prior Publication Data

US 2009/0143290 A1 Jun. 4, 2009

Related U.S. Application Data

(60) Division of application No. 11/273,593, filed on Nov. 14, 2005, now abandoned, which is a continuation of application No. PCT/CN2004/000473, filed on May 12, 2004.

(30) Foreign Application Priority Data

May 14, 2003 (CN) .................................. 03 1 16920

(51) Int. Cl.
*G01N 33/574* (2006.01)
(52) U.S. Cl. ......................................... 435/7.23; 435/7.1

(58) Field of Classification Search .................. 435/7.1, 435/7.23
See application file for complete search history.

(56) References Cited

FOREIGN PATENT DOCUMENTS

WO    WO 0153312 A1 * 7/2001

OTHER PUBLICATIONS

Jones (Pharmacogenomics Journal, 1:126-134, 2001).*
Tosatto et al (Current Pharmaceutical Design, 12:2067-2086, 2006).*
Skolnick et al. (Trends in Biotechnology 2000; 18: 34-39).*
Bowie et al. (Science 257: 1306-1310, 1990).*
Bult et al (QJNMMI, 53:325-335, 2009).*
Tockman et al (Cancer Res, 52:2711s-2718s, 1992).*
Xu et al (Biochem. Biophys. Res. Comm., 311:1057-1066, 2003).*

* cited by examiner

*Primary Examiner* — Misook Yu
*Assistant Examiner* — Brad Duffy
(74) *Attorney, Agent, or Firm* — Osha • Liang LLP (57) ABSTRACT

The invention has disclosed a new tumor suppressor protein HCRP1, the polynucleotide sequences encoding this polypeptides, and methods for production of the polypeptide using the recombinant technology. The tumor suppression protein, HCRP1, is obtained through the positional candidate cloning strategy. It locates in 8p22 region of human chromosome. The full length cDNA for HCRP1 is 1916 bp, which encodes a protein of 397 amino acids. When introduced into liver cancer cells, HCRP1 can inhibit the malignant transformation of liver cancer cells.

1 Claim, 1 Drawing Sheet

Fig. 3

TUMOR-INHIBITING PROTEIN AND THE USE THEREOF

CROSS-REFERENCE TO RELATED APPLICATIONS

This is a divisional application of U.S. patent application Ser. No. 11/273,593, filed on Nov. 14, 2005, now abandoned, which is a continuation of International application number PCT/CN2004/000473, filed May 12, 2004, which claims priority to Chinese application No. CN 03116920.1 filed May 14, 2003, the contents of these prior applications are herein incorporated in their entirety by reference.

FIELD OF THE INVENTION

The present invention relates to the field of biological technology. More specifically, this invention is directed to a new tumor suppressor protein and the encoding polynucleotide thereof. This invention is also directed to the use and preparation of the polynucleotide and polypeptide. The polypeptide of this invention is a tumor suppressor protein that can inhibit malignant tumor proliferation.

BACKGROUND OF THE INVENTION

Malignant tumor, as a vital disease threatening the human health, is the second leading cause of mortality. Statistics shows that the top 5 malignant cancers contributing to death in China are stomach cancer, liver cancer, lung cancer, esophagus cancer and large intestine cancer. Tumor is the abnormal hyperplasia of cell. Cancer cells have gained the ability of uncontrolled growth and reproduction, thereby invading adjacent normal tissue and metastasizing to distant tissues or organs. Tumorigenesis is a complex and gradual process with multiple factors and steps.

Carcinogenesis of normal cells is related to alter genetic characteristics. Generally, genes directly associated with cancer are often divided into two categories: (i) cancer-causing genes, called oncogenes, which are involved in cell growth, metabolism, promotion and regulation of cell proliferation and differentiation and (ii) cancer-inhibiting genes, called tumor suppressor genes, which are related to inhibition of neoplastic cell transformation and tumorigenesis. These two classes of genes are targets of the mutations that convert normal cells to cancer ones. Mutations including point mutation, loss or shift of DNA fragments of these two classes of genes can lead to uncontrolled cell growth and neoplasm.

Surgery, radiotherapy and chemotherapy have been the three main models of tumor therapy in recent years. These therapeutic methods are based on killing tumor cells directly, and it is difficult to completely eliminate all the cancer cells and is prone to injuring normal tissue, especially to impairing organism immune system and affecting native cellular immunity. With the development of modern molecular biology and genetic engineering technology, biological therapy has become the fourth model of tumor therapy. Deregulation of the dynamic balance, which exists between tumor and organism defense system under normal conditions, causes tumor proliferation and dissemination. Tumor biological therapy refers to the treatment of organism by regulating it's biological reaction according to tumor host defense mechanism or using biological reagent, which results in the tumor cell inhibition or death. Take tumor suppressor gene therapy for example, it restores the function of the tumor suppressor by transfer of tumor suppressor genes which are inactivated or absent in tumor cells, thereby exerting inhibitory or therapeutic effect on proliferation and metastasis of malignant tumor.

In order to effectively cure and prevent tumor, there is an urgent need in the art to provide more tumor suppressor proteins and associated activators/inhibitors.

SUMMARY OF INVENTION

The aim of the present invention is to offer a novel tumor-inhibiting protein and its fragments, analogs and derivatives.

The second aim of the present invention is to offer the polynucleotides that encode these polypeptides.

The third aim of the present invention is to offer the method of producing these polypeptides and the application of these polypeptides and coding sequences.

In the 1st aspect of the invention, it provides an isolated tumor-inhibiting protein which is selected from the group consisting of:

(a) a polypeptide having the amino acid sequence of SEQ ID NO: 2;

(b) a polypeptide which is derived from polypeptide (a) by substitution, deletion or insertion of one or more amino acid residues and which has the function of inhibiting tumor (such inhibiting the malignant proliferation of liver cancer cell).

Preferably, the polypeptide has the amino acid sequence of SEQ ID NO: 2.

In the 2nd aspect of the invention, it provides an isolated polynucleotide encoding the above polypeptide of invention. Preferably, the polynucleotide encodes a polypeptide comprising the amino acid sequence of SEQ ID NO: 2. More preferably, the polynucleotide is selected from the group consisting of:

(c) full-length sequence of SEQ ID NO: 1; and (d) nucleotides 151-1341 of SEQ ID NO: 1.

In the 3rd aspect, it provides a vector comprising the above polynucleotide, and a host cell transformed with the vector or polynucleotide.

In the 4th aspect, it provides a method for producing a tumor-inhibiting protein, which comprises:

(a) culturing the above host cell under the conditions suitable for the expression of protein;

(b) isolating the tumor-inhibiting protein from the culture.

In the 5th aspect, it provides an antibody which specifically bind to the above tumor-inhibiting protein. Also provided are nucleic acid molecules for detection, which comprising at least consecutive 10 nucleotides to the full-length sequence, or preferably consecutive 15-1000 nucleotides of the above polynucleotide.

In the 6th aspect, it provides a pharmaceutical composition comprising a safe and efficient amount of the tumor-inhibiting protein or polynucleotide of the invention and a pharmaceutically acceptable carrier. The pharmaceutical composition can be used to treat diseases such as tumors and abnormal proliferation of cells. The invention also provides the uses of the tumor-inhibiting protein and polynucleotide of the invention in the preparation of medicines for treating tumor, especially liver cancer.

In the 7th aspect, it provides a method for detecting liver cancer comprising: detecting amount of HCRP1 transcripts in a sample of liver cell, wherein if the amount of HCRP1 transcripts in the sample is than that in the normal control, it indicates that the possibility of existence of hepatocarcinoma cell in the sample is higher than that in the normal tissue. It also provides a diagnostic kit for detection of liver cancer. This diagnostic kit contain anti-HCRP1 specific antibody and reaction solutions

DETAILED DESCRIPTION OF INVENTION

The inventors of the present invention have isolated a new tumor suppressor-associated gene HCRP1 by positional candidate cloning. This gene localizes in 8p22 region of the human chromosome, where loss of heterozygosity (LOH) occurs high frequently in many tumors and a hot spot for cloning of tumor suppressor. Full-length sequencing indicated that HCRP1 cDNA is 1916 bp, which comprises a complete open reading frame (nucleotides 151-1341) encoding a 397aa tumor suppressor protein named HCRP1 (SEQ ID NO:2).

In the invention, the distribution of HCRP1 gene expression in human tissue was also examined using Northern blotting analysis of HCRP1 mRNA in 8 human normal tissues, which revealed that HCRP1 gene was highly expressed in liver, moderately in lung, spleen, muscle and testis, yet minimally or not expressed in brain, heart and stomach. Additionally, soft agar colony formation assay indicated that high expression of HCRP1 gene could inhibit colony formation of SMMC-7721 cell in soft agar, while knock-down of HCRP1 gene expression by antisense cDNA remarkably promoted colony formation of SMMC-7721 cell in soft agar. These results suggested that HCRP1 could inhibit the malignant proliferation of HCC cells. In viva tumorigenecity assay in nude mice also suggested that HCRP1 could inhibit tumor growth.

The term "isolated" means that the material is removed from its original environment (e.g., the natural environment if it is naturally occurring). For example, a naturally-occurring polynucleotide or polypeptide present in a living animal is not isolated, but the same polynucleotide or polypeptide, separated from some or all of the coexisting materials in the natural system, is isolated.

As herein described, "isolated tumor-inhibiting protein or polypeptide" or "isolated HCRP1" refers to HCRP1 polypeptide essentially free from contaminating cellular components, such as carbohydrate, lipid, or other proteinaceous impurities associated with the polypeptide in nature. The technical personnel in the art can purify HCRP1 protein with standard protein purification techniques. Essentially purified polypeptide forms a single main band on a non-reductive PAGE gel.

As used herein, "the polypeptide of invention" means tumor-inhibiting protein HCRP1 or its fragments, derivatives and analogues having the tumor-inhibiting function.

The polypeptides of the present invention can be recombinant polypeptides, nature polypeptides, synthesized polypeptides, and preferably recombinant polypeptides. The polypeptides of the present invention can be naturally purified products, or chemically synthesized products, or recombinant products from prokaryotic or eukaryotic hosts (e.g. bacteria, yeast, higher plant, insect or mammalian cell). The polypeptides of the present invention can be glycosylated or non-glycosylated according to the different hosts used. The polypeptide of invention may or may not comprise the starting Met residue.

The invention further comprises the fragments, derivatives and analogues of HCRP1. As used in the invention, the terms "fragment", "derivative" and "analogue" mean the polypeptide that essentially retains the same biological functions or activity of HCRP1 protein of the invention. The fragment, derivative or analogue of the polypeptide of invention may be (i) one in which one or more of the amino acid residues are substituted with a conserved or non-conserved amino acid residue (preferably a conserved amino acid residue) and such substituted amino acid residue may or may not be one encoded by the genetic code, or (ii) one in which one or more of the amino acid residues include a substituent group, or (iii) one in which the mature polypeptide is fused with another compound, such as a compound to increase the half-life of the polypeptide (for example, polyethylene glycol), or (iv) one in which the additional amino acids are fused to the mature polypeptide, such as a leader or secretary sequence or a sequence which is employed for purification of the mature polypeptide or a proprotein sequence, e.g., a fusion protein formed with IgC fragment. Such fragments, derivatives and analogs are deemed to be within the scope of those skilled in the art from the teachings herein.

The polynucleotide of invention may be in the forms of DNA and RNA. DNA includes cDNA, genomic DNA, and synthetic DNA, etc., in single strand or double strand form. A single strand DNA may be an encoding strand or non-encoding strand. The coding sequence for mature polypeptide may be identical to the coding sequence shown in SEQ ID NO: 1, or is a degenerate sequence. As used herein, the term "degenerate sequence" means an sequence which encodes a protein comprising the sequence of SEQ ID NO: 2 and which has a nucleotide sequence different from the coding region in SEQ ID NO: 1.

The sequences encoding the mature HCRP1 polypeptide include those encoding only the mature polypeptide, those encoding mature polypeptide plus various additional encoding sequence, the encoding sequence for mature polypeptide plus the non-encoding sequence and optional additional encoding sequence.

The term "polynucleotide encoding the polypeptide" includes the polynucleotide encoding the polypeptide and the polynucleotide comprising additional and/or non-encoding sequence.

The invention further relates to the variants of the hereinabove polynucleotides which encode a polypeptide having the same amino acid sequence of invention, or its fragment, analogue and derivative. The variant of the polynucleotide may be a naturally occurring allelic variant of the polynucleotide or a non-naturally occurring variant of the polynucleotide. Such nucleotide variants include substitution, deletion, and insertion variants. As known in the art, the allelic variant is a substitution form of polynucleotide, which may be a substitution, deletion, and insertion of one or more nucleotides without substantially changing the functions of the encoded polypeptide.

The present invention further relates to polynucleotides, which hybridize to the hereinabove-described sequences, if there is at least 50%, preferably at least 70%, and more preferably at least 80% identity between the sequences. The present invention particularly relates to polynucleotides, which hybridize under stringent conditions to the polynucleotides of the invention. As herein used, the term "stringent conditions" means the following conditions: (1) hybridization and washing under low ionic strength and high temperature, such as 0.2×SSC, 0.1% SDS, 60° C.; (2) hybridization after adding denaturants, such as 50% (v/v) formamide, 0.1% bovine serum/0.1% FICOLL™, 42° C.; or (3) hybridization of two sequences sharing at least 95%, preferably 97% homology. Further, the polynucleotides which hybridize to the hereinabove described polynucleotides encode a polypeptide which retains the same biological function or activity as the mature polypeptide shown in SEQ ID NO: 2.

The invention also relates to nucleic acid fragments hybridized with the hereinabove sequence. As used in the present invention, the length of the "nucleic acid fragment" is at least 15 bp, preferably at least 30 bp, more preferably at least 50 bp, and most preferably at least 100 bp. The nucleic acid fragment can be used in the amplification techniques of nucleic acid, e.g., PCR, so as to determine and/or isolate the polynucleotide encoding HCRP1 protein.

These polypeptide and polynucleotide of the invention is preferably provided in an isolated form or more preferably is purified to be homogenous.

The full-length HCRP1 nucleotide sequence or its fragment can be prepared by PCR amplification, recombinant method and synthetic method. For PCR amplification, one can obtain the sequences by designing primers based on the nucleotide sequence disclosed herein, especially the ORF, and using cDNA library commercially available or prepared by routine techniques in the art as a template. When the sequence is long, it is usually necessary to perform two or more PCR amplifications and link the amplified fragments together correctly.

Once the sequence is obtained, one can produce lots of the sequences by recombinant methods. Usually, the sequence is cloned into a vector which is then transformed into a host cell. The sequence is isolated from the amplified host cells using conventional techniques.

Further, the sequence can be synthesized, especially when the fragment is short. Typically, several small fragments are synthesized and linked together to obtain a long sequence.

It is completely feasible to chemically synthesize the DNA sequence encoding the protein of invention, or the fragments or derivatives thereof. Then, the DNA sequence can be introduced into the various DNA molecules (such as vectors) and cells available in the art. In addition, the mutation can be introduced into the protein sequence by chemical synthesis.

The recombinant human HCRP1 polypeptides can be expressed or produced by the conventional recombinant DNA technology, using the polynucleotide sequence of invention. Generally, it comprises the following steps:

(1) transfecting or transforming the appropriate host cells with the polynucleotide or its variants encoding HCRP1 polypeptide of the invention or the vector containing the polynucleotide, (2) culturing the host cells in an appropriate medium;

(3) isolating or purifying the protein from the medium or cells.

In the present invention, the polynucleotide sequences encoding HCRP1 may be inserted into a recombinant expression vector.

In the present invention, the polynucleotide sequences encoding HCRP1 may be inserted into a recombinant expression vector. The term "expression vector" refers to a bacterial plasmid, bacteriophage, yeast plasmid, plant virus or mammalian cell virus, such as adenovirus, retrovirus or any other vehicle known in the art. Vectors suitable for use in the present invention include, but are not limited to, the T7-based expression vector for expression in bacteria, the pMSXND expression vector for expression in mammalian cells and baculovirus-derived vectors for expression in insect cells. On the whole, any plasmid or vector can be used to construct the recombinant expression vector as long as it can replicate and is stable in the host. One important feature of expression vector is that the expression vector typically contains an origin of replication, a promoter, a marker gene as well as the translation regulatory components.

The methods known by the artisans in the art can be used to construct an expression vector containing the DNA sequence of HCRP1 and appropriate transcription/translation regulatory components. These methods include in vitro recombinant DNA technique, DNA synthesis technique, in vivo recombinant technique and so on (Sambrook, et al. Molecular Cloning, a Laboratory Manual, Cold Spring Harbor Laboratory. New York, 1989). The DNA sequence is efficiently linked to the proper promoter in an expression vector to direct the synthesis of mRNA. The exemplary promoters are lac or trp promoter of *E. coli*; PL promoter of lambda phage; eukaryotic promoter including CMV immediate early promoter, HSV thymidine kinase promoter, early and late SV40 promoter, LTRs of retrovirus and some other known promoters which control the gene expression in the prokaryotic cells, eukaryotic cells or virus. The expression vector may further comprise a ribosome-binding site for initiating the translation, transcription terminator and the like.

Further, the expression vector preferably comprises one or more selective marker genes to provide a phenotype for the selection of the transformed host cells, e.g., the dehydrofolate reductase, neomycin resistance gene and GFP (green flurencent protein) for eukaryotic cells, as well as tetracycline or ampicillin resistance gene for *E. coli*.

The vector containing the DNA sequence and proper promoter or regulatory elements can be transformed into appropriate host cells to express the protein.

The "host cell" includes prokaryote, such as bacteria; primary eukaryote, such as yeast; advanced eukaryotic, such as mammalian cells. The representative examples are bacterial cells, such as *E. coli, Streptomyces, Salmonella typhimurium*; fungal cells, such as yeast; plant cells; insect cells such as *Drosophila* S2 or Sf9; animal cells such as CHO, COS or Bowes melanoma, etc.

Transcription of the polynucleotide of invention in higher eukaryotes is increased by inserting an enhancer sequence into the vector. Enhancers are cis-acting elements of DNA, usually about from 10 to 300 bp that act on a promoter to increase the gene transcription. Examples include the SV40 enhancer on the late side of the replication origin 100 to 270 bp, the polyoma enhancer on the late side of the replication origin, and adenovirus enhancers.

The skilled in the art know clearly how to select appropriate vectors, promoters, enhancers and host cells.

Recombinant transformation of host cell with the DNA sequence of invention might be carried out by conventional techniques well known to those skilled in the art. Where the host is prokaryotic such as *E. coli*, the competent cells, which are capable of DNA uptake, can be prepared from cells harvested after exponential growth phase and subsequently treated by the CaCl$_2$ method using procedures well known in the art. Alternatively, MgCl$_2$ can be used. The transformation can also be carried out by electroporation, if desired. When the host is an eukaryote, such methods of transfection of DNA as calcium phosphate co-precipitates, conventional mechanical procedures such as micro-injection, electroporation, or liposome-mediated transfection may be used.

The transformants are cultured using conventional methods to express the polypeptides of the invention. According to the used host cells, the medium for cultivation can be selected from various conventional mediums. The host cells are cultured under a condition suitable for its growth until the host cells grow to an appropriate cell density. Then, the selected promoter is induced by appropriate means (e.g., temperature shift or chemical induction) and cells are cultured for an additional period.

In the above methods, the recombinant polypeptide may be included in the cells, or expressed on the cell membrane, or secreted out of the cell. If desired, the physical, chemical and other properties can be utilized in various isolation methods to isolate and purify the recombinant protein. These methods are well-known to those skilled in the art and include, but are not limited to conventional renaturation treatment, treatment by protein precipitant (such as salt precipitation), centrifugation, cell lysis by osmosis, sonication, supercentrifugation, molecular sieve chromatography or gel chromatography, adsorption chromatography, ion exchange chromatography, HPLC, and any other liquid chromatography, and the combination thereof.

The recombinant HCRP1 proteins or polypeptides have various uses including, but not to be limited to: treat diseases which are caused by the loss or depression of the HCRP1 protein function (such as liver cancer); screening antibodies, polypeptides or other ligands which can activate or inhibit the function of HCRP1 protein. Screening the polypeptide library with expressed recombinant HCRP1 protein will help us to find the polypeptides with therapeutic potential, which can inhibit or activate the function of HCRP1.

The invention also provides the method for screening compounds so as to identify agents which improve HCRP1 protein (agonists) or repress HCRP1 protein (antagonists). The antagonists of HCRP1 protein include the screened antibodies, compounds, receptor deletants and analogues. The antagonists of HCRP1 protein can bind to HCRP1 protein and eliminate its function, or inhibit the production of HCRP1, or bind to the active site of the polypeptide so that the polypeptide can not function biologically.

The polypeptide of invention can be directly used for the treatment of diseases, e.g., various malignant tumors, abnormal cell proliferation.

The polypeptide, and its fragment, derivative, analogue or cells can be used as antigens to produce antibodies. These antibodies may be polyclonal or monoclonal antibodies.

According to the invention, the polypeptides, or its antagonists may be employed in combination with a suitable pharmaceutical carrier. Such a carrier includes but is not limited to water, glucose, ethanol, salt, buffer, glycerol, and combinations thereof. Such compositions comprise a safe and effective amount of the polypeptide or antagonist, as well as a pharmaceutically acceptable carrier or excipient which does not influence the effect of the drug. These compositions can be used for treatment of disease.

The invention also provides a pharmaceutical pack or kit comprising one or more containers filled with one or more of the ingredients of the pharmaceutical compositions of the invention. Associated with such container (s) can be a notice in the form prescribed by a governmental agency regulating the manufacture, use or sale of pharmaceuticals or biological products, which notice reflects approval by the agency of manufacture, use or sale for human administration. In addition, the polypeptides of the invention may be employed in conjunction with other therapeutic compounds.

The pharmaceutical compositions may be administered in a convenient manner such as by the topical, intravenous, intraperitoneal, intramuscular, subcutaneous, intranasal or intradermal routes. The HCRP1 protein is administered in an amount which is effective for treating and/or prophylaxis of the specific indication. The amount of HCRP1 protein administrated on patient will depend upon various factors, such as delivery methods, the subject health, and the like, and is within the judgment of the skilled clinician.

HCRP1 polynucleotides also have many therapeutic applications. Gene therapy technology can be used in the therapy of the abnormal cell proliferation, development or metabolism, which is caused by the loss of HCRP1 expression or the expression of abnormal or non-active HCRP1. The recombinant gene therapy vectors can be used to cure the diseases caused by the abnormal expression or activity of HCRP1. The expression vectors derived from virus, such as retrovirus, adenovirus, adeno-associated virus, herpes simplex virus, parvovirus, and so on, can be used to introduce the HCRP1 gene into the cells. The methods for constructing a recombinant virus vector harboring HCRP1 gene are described in the literature (Sambrook, et al.). In addition, the recombinant HCRP1 gene can be packed into liposome and then transferred into the cells.

The methods for introducing the polynucleotides into tissues or cells include: directly injecting the polynucleotides into tissue in the body, in vitro introducing the polynucleotides into cells with vectors, such as virus, phage, or plasmid, and then transplanting the cells into the body.

The invention also provides the antibodies against the determinants of HCRP1 protein. These antibodies include, but are not limited to, polyclonal antibody, monoclonal antibody, chimeric antibody, single-chain antibody, Fab fragment and the fragments produced by Fab expression library. The antibody against HCRP1 protein can be used in immunohistochemical method to detect the presence of HCRP1 protein in the biopsy specimen.

Antibodies can also be designed as an immunotoxin targeting at the particular site in the body. For example, a monoclonal antibody having high affinity to HCRP1 protein can be covalently bound to bacterial or plant toxins, such as diphtheria toxin, ricin, and ormosine.

The polyclonal antibodies can be prepared by immunizing animals, such as rabbit, mouse, and rat, with HCRP1 protein. Various adjuvants, e.g., Freund's adjuvant, can be used to enhance the immunization.

The techniques for producing HCRP1 protein monoclonal antibodies include the hybridoma technique (Kohler and Milstein. Nature, 1975, 256:495-497). The chimeric antibody comprising a constant region of human origin and a variable region of non-human origin can be produced using the conventional method in the art (Morrison et al, PNAS, 1985, 81:6851). Furthermore, the techniques for producing single-chain antibody (U.S. Pat. No. 4,946,778) are also useful for preparing the single-chain antibody against HCRP1 protein.

The invention further provides diagnostic assays for quantitative and in situ measurement of HCRP1 protein level. These assays are well known in the art and include FISH assay and radioimmunoassay. The level of HCRP1 protein detected in the assay can be used to illustrate the importance of HCRP1 protein in diseases and to determine the diseases associated with HCRP1 protein.

The polynucleotide encoding HCRP1 protein can be used in the diagnosis of HCRP1 protein related diseases. The polynucleotide encoding HCRP1 can be used to detect whether HCRP1 is expressed or not, and whether the expression of HCRP1 is normal or abnormal, e.g., in the case of diseases. HCRP1 DNA sequences can be used in the hybridization with biopsy samples to determine the expression of HCRP1. The hybridization methods include Southern blotting, Northern blotting and in situ blotting, etc., which are public and sophisticated techniques. The corresponding kits are commercially available. A part of or all of the polynucleotides of the invention can be used as probe and fixed on a microarray or DNA chip for analysis the differential expression of genes in tissues and for the diagnosis of genes. The HCRP1 specific primers can be used in RNA-polymerase chain reaction and in vitro amplification to detect the transcripts of HCRP1.

Further, detection of the mutation of HCRP1 gene is useful for the diagnosis of HCRP1 protein related diseases. The mutation forms of HCRP1 include site mutation, translocation, deletion, rearrangement and any other mutations compared with the wild-type HCRP1 DNA sequence. The conventional methods, such as Southern blotting, DNA sequencing, PCR and in situ blotting, can be used to detect mutation. Moreover, mutation sometimes affects the expression of protein. Therefore, Northern blotting and Western blotting can be used to indirectly determine whether the gene is mutated or not.

The main advantages of the present invention are as follows:

1. The invention provides a brand-new tumor suppressor protein named as HCRP1, which is of great significance to expand our understanding of the molecular mechanism of tumorigenesis and tumor development.

2. This invention discovers that HCRP1 gene can inhibit soft agar colony formation and decrease the tumorigenecity in nude mice, which indicates that HCRP1 is involved in negative regulation of cell growth and that HCRP1 can be applied clinically, as drug or drug target sequence, to the early diagnosis and treatment of tumor-associated diseases.

3. Expression of HCRP1 gene in normal human tissues is tissue-specific. It is highly expressed in liver, moderately expressed in lung, spleen, muscle and testis, while minimally or not expressed in brain, heart and stomach, which indicates that HCRP1 gene plays an important role in liver tissue and it can be applied to diagnosis and treatment of liver, lung, spleen and testis-associated diseases.

4. As HCRP1 of the present invention has the native amino acid sequence from human itself, it is predicted to have higher efficiency and lower side-effects when applied to human compared with its homologues from other species (e.g. less or even no immunogenicity in human body).

The invention is further illustrated by the following examples. It is appreciated that these examples are only intended to illustrate the invention, but not to limit the scope of the invention. For the experimental methods in the following examples, they are performed under routine conditions, e.g., those described by Sambrook. et al. in Molecule Clone: A Laboratory Manual, New York: Cold Spring Harbor Laboratory Press, 1989, or as instructed by the manufacturers, unless otherwise specified.

Example 1

Cloning of Full-Length cDNA for HCRP1 Gene

According to the positional candidate cloning strategy and human genomic sequence database, primers P1 (SEQ ID NO: 3) and P2 (SEQ ID NO: 4) were designed to amplify the HCRP1 cDNA from the human liver cDNA library (GIBCO BRL). The polymerase chain reaction (PCR) was performed with pre-denaturing for 2 min and 35 cycles of 94° C. for 30 s, 50° C. for 30 s, and 72° C. for 2 min. The PCR product was purified by using low melting agarose gel (see Sambrook, J., Fritsh, E. F., and Maniais, T., Molecular Cloning, Cold Spring Harbor Laboratory Press, 1989). Sequencing of the full-length cDNA was conducted by Bioasia, Co, Ltd (Shanghai, China).

The obtained 1916 by full-length cDNA (SEQ ID NO:1) comprises a whole protein-encoding region (from 151 by to 1314 bp), which codes for a protein consisting of 397 amino acids (SEQ ID NO:2).

Example 2

RNA Blot Analysis of HCRP1 Expression in Multiple Human Tissues

Multiple-tissue RNA blot membrane fixed with 8 different normal human tissues was placed in to a hybridization tube. 5 mL pre-hybridization solution (Kingrace) was added and the mixture was pre-hybridized at 65° C. for 30 minutes. Then the denatured probe of HCRP1 was added, which was randomly labeled with $^{32}$P (Random Primer DNA Labeling Kit, Takara), and hybridized overnight at 65° C. The blot membrane was washed with resin buffer I (0.3M NaCl, 0.03M citrate sodium (PH7.0), 0.05% sodium dodecyl sulfate) at room temperature; and then washed twice (20 min each) at 50° C. with resin buffer II (15 mM NaCl, 1.5M citrate sodium (PH7.0), 0.1% sodium dodecyl sulfate (SDS)). After that, the hybridized film was exposed to X-ray and radioautographed at −70° C.

Figure 1:
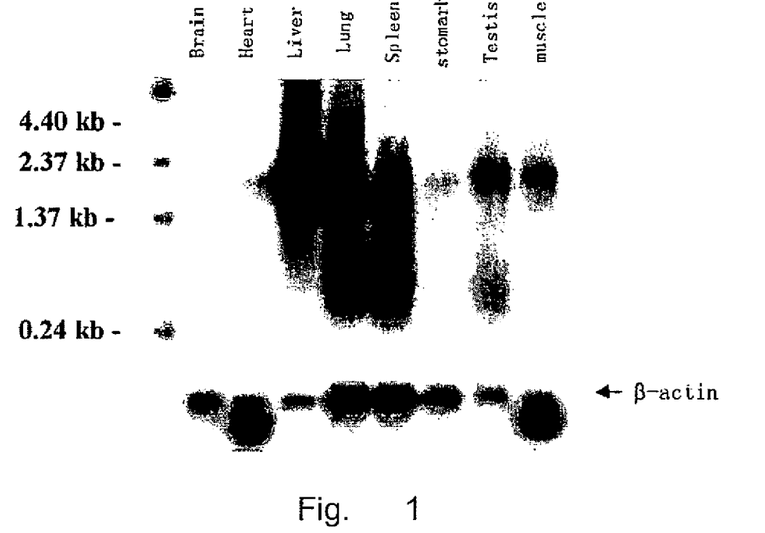
FIG. 1 illustrates Northern Blotting analysis of HCRP1 mRNA expression in multiple human tissues. It showed that HCRP1 gene was highly expressed in normal human liver tissue.

As shown in FIG. 1, HCRP1 gene was highly expressed in liver, moderately in lung, spleen, testis and muscle, yet minimally or not expressed in brain, heart and stomach. The size of the expression product was about 2 Kb.

Example 3

Construction of Eukaryotic Expression Vector of HCRP1 Gene and Expression and Measurement of HCRP1 Protein Primer P3 (SEQ ID NO:5) and primer P4 (SEQ ID NO:6) were designed according to the cDNA sequence of HCRP1 with the restriction endonuclease site of XbaI and EcoRI added to 5' site of the primers, respectively. PCR reaction was performed by using the verified sequence of HCRP1 as template. The PCR product was recovered from the low melting agarose gel and then was digested for an hour with restriction enzyme XbaI and EcoRI (Takara, Co, Ltd.), followed by purification again. The vector pCMV-Tag2A (Stratagene) was also digested for an hour with the same restriction enzyme XbaI and EcoRI, followed by purification on low melting agarose gel. The two recovered products were ligated with T4 DNA ligase (Takara) at 16° C. overnight and then were introduced into E. Coli DH5α. The recombinant HCRP1 plasmid was obtained by screening and designated as pcDNA3-Flag-HCRP1. Primer P5 (SEQ ID NO:7) and primer P6 (SEQ ID NO:8) were synthesized according to cDNA sequence of HCRP1 with the restriction endonuclease site of HidIII and SalI added to 5' end of the primers, respectively. The recombinant plasmid containing antisense HCRP1 cDNA was obtained with the same method described above, i.e., HCRP1 gene was amplified by PCR and cloned into plasmid pcDNA3 to give the recombinant plasmid through screening, which was designated as pcDNA3-HCRP1(−).

HCC SMMC-7721 cells were cultured in RPMI 1640 (Gibco BRL) containing 10% fetal bovine serum (Gibco BRL). $2\times10^5$ cells were seeded into 60-mm culture dish and incubated at 37° C. After 24 hours, cells were transfected with 1.5 ug of pcDNA3, pcDNA3-Flag-HCRP1 or pcDNA3-HCRP1(−) plasmid using 10 ul of lipofectamine (Gibco BRL). 24 hours after transfection, cells were changed into fresh medium with 700 ug/mL G418 (Gibco BRL), and cultured for further 3 weeks during which the medium was changed every 3 days. The monoclones were selected and cultured. The positive monoclones stably expressing HCRP1 protein were designated as SMMC-7721/HCRP1(+); the cell line stably transfected with antisense HCW1 plasmid were named as SMMC-7721/HCRP1(−); and the cell line stably transfected with pcDNA3 were named as SMMC-7721/con.

Example 4

HCRP1 Inhibited Colony Formation of HCC Cell Line SMMC-7721 in Soft Agar

SMMC-7721/con, SMMC-7721/HCRP1(+) and SMMC-7721/HCRP1(−) cells were cultured in RPMI1640 medium containing 10% FBS and 700 ug/mL G418 under 37° C., 5% $CO_2$. Exponentially growing cells were trypsinized and mixed with complete medium containing 0.35% agar and overlaid on 0.6% agar in 6-well plates ($2\times10^4$ cells/well). The cultures were maintained in a 37° C., 5% $CO_2$ incubator for 3 weeks. Colonies containing more than 50 cells were subsequently counted and photographed.

Figure 2:
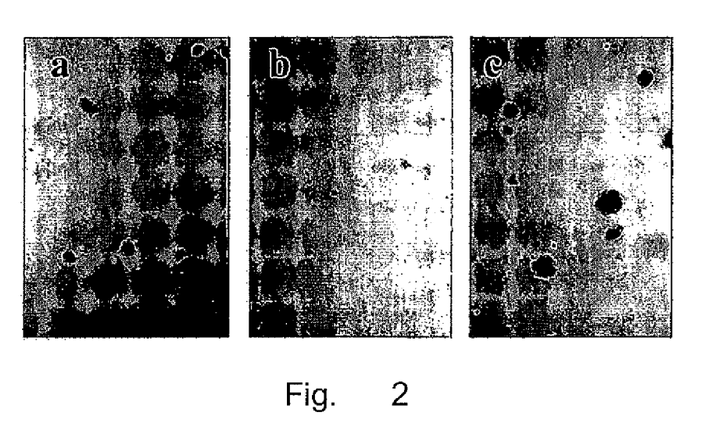
FIG. 2 illustrates detection of HCRP1 inhibiting malignant proliferation of HCC cells by soft agar colony formation assay. (a) SMMC-7721 cell line stably transfected with pcDNA3 blank vector was used as control; (b) Colony formation was inhibited in SMMC-7721 cell line stably transfected with pcDNA3-HCRP1; (c) Colony formation was significantly enhanced in SMMC-7721 cell line stably transfected with the antisense HCRP1 cDNA.

The results showed that the colony formation of SMMC-7721/HCRP1 (+) was less than that of SMMC-7721/con cells, while colony formation (including the size and amount of the colony) of SMMC-7721/HCRP1(−) in soft agarose was more than that of control cells (FIG. 2). These results suggested that HCRP1 could inhibit the malignant proliferation of HCC cells in soft agar.

Example 5

HCRP1 Inhibited the Tumorigenesity of SMMC-7721 HCC Cells in Nude Mice

The SMMC-7721/con, SMMC-7721/HCRP1(+), and SMMC-7721/HCRP1 (−) cells at the logarithm growth period were trypsinized, washed twice with serum free medium and suspended in PBS. Then, the cells were injected s.c. into both flanks of nude mice (BALB/C, male, 6-week old) with $2\times10^6$/100 uL per site. The nude mice were sacrificed 11 weeks after injection and tumors were photographed and weighed.

Figure 3:
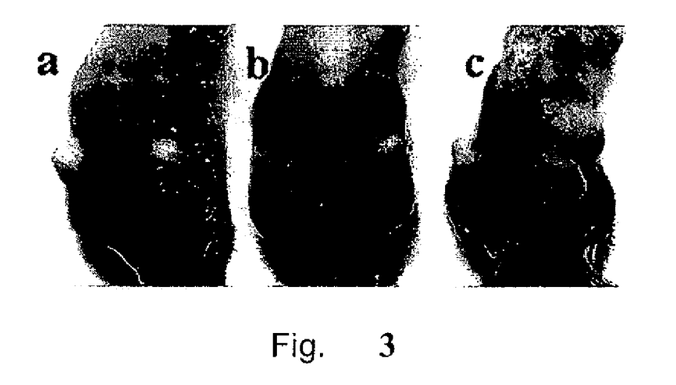
FIG. 3 illustrates functional analysis of HCRP1 for inhibiting malignant proliferation of HCC cells in nude mice by in vivo tumorigenecity assay. (a) SMMC-7721 cell line stably transfected with pcDNA3 blank vector was used as control; (b) Tumorigenecity was reduced in SMMC-7721 cell line stably transfected with pcDNA3-HCRP1; (c) Tumorigenecity was significantly enhanced in SMMC-7721 cell line stably transfected with the antisense HCRP1 cDNA.

As shown in FIG. 3, SMMC-7721/HCRP1 (+) cells formed smaller tumor than SMMC-7721/con control group, yet SMMC-7721/HCRP1(−) formed larger tumor than SMMC-7721/con control group, which was consistent with results of soft-agar colony formation assay, indicating that HCRP1 could inhibit neoplasm.

Example 6

Expression and Purification of Recombinant HCRP1 Protein

HCRP1 gene was inserted into pET24a (Novagen) expression vector at the restriction sites of NheI and XhoI. The recombinant plasmid was transformed into *E. coli* BL21-DE3 and amplified. Plasmid DNA was then extracted and identified by digestion with the corresponding restriction endonucleases. The insert of HCRP1 cDNA was further verified by DNA sequencing.

Identified HCRP1 transformant was then inoculated into 5 L LB medium (each liter contains 10 g Polypepton, 5 g yeast extract and 10 g NaCl) at a ratio of 1:20, and incubated for about 3 hours at 37° C. until $OD_{600}$ reached 0.6-0.8. The culture was induced by adding IPTG to a final concentration of 0.5 mM for additional 3-4 hours.

The cell pellet was harvested by centrifuge at 600 rpm for 10 minutes. The pellet was resuspended in TEG solution containing 50 mM NaCl (10 mL/g pellet), and sonicated for 12×30 seconds at an interval of 1 minute. 10% deoxycholate sodium was added to a final concentration of 2% and the suspension was stirred for 10 minutes. The precipitate was collected by centrifuge at 13,000 rpm for 10 minutes and resuspended in TEG containing 50 mM NaCl. 10% deoxycholate sodium was added to the suspension to a final concentration of 2%. The suspension was stirred and centrifuged at 13,000 rpm, each for 10 minutes. This was repeated twice. The final precipitate was HCRP1 inclusion body, which was kept at 4° C. The inclusion body protein was separated on SDS PAGE. After gel staining, the slices containing His-HCRP1 fusion protein was excised, and then the fusion protein was isolated from the gel using the Electro-Eluter (Bio-Rad) according to the manufacture's instruction.

Example 7

Preparation of Anti-HCRP1 Antibody 300 ug purified HCRP1 fusion protein in Example 6 was dissolved in 0.5 mL PBS, and mixed vigorously with equal volume of complete Freud's adjuvant. Then the mixture was injected subcutaneously into the backs of 2.0 kg New Zealand white rabbit at multiple sites. On the third day, the rabbit was re-injected with the same amount of HCRP1 fusion protein mixed with complete Freud's adjuvant. At 28th day, the rabbit was injected with the same amount of HCRP1 fusion protein mixed with incomplete Freud's adjuvant to enhance the immunity. One week after the last injection, the rabbit was sacrificed and the blood was collected by carotid puncture. The blood was maintained at 37° C. for 3 hours, and then laid-aside overnight at 4° C. to allow the serum precipitate completely. The serum was collected by centrifuge and sub-packaged, stocked at −70° C.

Example 8

Immunohistochemistry Analysis of HCRP1 Expression in Clinical HCC Tissue Samples The sections of paraffin-embedding clinical HCC tissue samples (6-10 μm) were soaked in xylene for 3×10 minutes and then incubated in xylene/100% ethanol for 15 minutes. The samples were rehydrated gradiently by placing in 95%, 80%, 70%, 50%, 30% ethanol and deionized $H_2O$ for 5 minutes each. The sections were then balanced in PBS solution for 15 minutes. After that, the sections were blocked in PBS solution supplemented with 4% BSA and 0.5% normal sheep serum for 1 hour at room temperature. Thereafter, the HCRP1-specific antibody prepared in Example 7 was diluted in the blocking buffer at a ratio of 1:200, and incubated overnight at 4° C. After three rinses in PBS for 10 minutes each, the sections were incubated for 30-60 minutes at room temperature with the second antibody (sheep-anti-rabbit IgG) diluted 1:200 in blocking buffer. Immediately afterwards, the sections were stained and observed under microscopy.

The results indicated that in 38 of 47 HCC tissue samples, the expression of HCRP1 protein was not detectable or significantly down-regulated while HCRP1 was expressed in the corresponding adjacent noncancerous tissues. Additionally, the expression of HCRP1 was detected in all the samples of normal liver tissue near the hepatic hemangioma. This further demonstrated that HCRP1 protein was expressed in the normal liver tissue, yet negative or significantly down-regulated in HCC tissues. The expression of HCRP1 complies with the expression model of tumor suppressor protein, suggesting that HCRP1 can not only be applied in the treatment of tumor, but can be further applied into diagnosis of liver cancer.

All the documents cited herein are incorporated into the invention as reference, as if each of them is individually incorporated. Further, it would be appreciated that, in the above teaching of the invention, the skilled in the art could make certain changes or modifications to the invention, and these equivalents would still be within the scope of the invention defined by the appended claims of the present application.

What is claimed is:

1. A method for detecting liver cancer comprising:

detecting an amount of a gene product of HCRP1 in a sample of liver cells from a test subject and an amount of the gene product of HCRP1 in a noncancerous liver tissue, wherein the gene product is an HCRP1 protein comprising the sequence of SEQ ID NO:2, wherein the detecting is performed using an antibody that binds the HCRP1 protein; and comparing the amount detected in the sample from the test subject with the amount detected in the noncancerous liver tissue, whereby hepatocellular carcinoma is indicated if the amount detected in the sample from the test subject is less than the amount detected in the noncancerous liver tissue.

* * * * *

SEQUENCE LISTING

```
<160> NUMBER OF SEQ ID NOS: 8

<210> SEQ ID NO 1
<211> LENGTH: 1916
<212> TYPE: DNA
<213> ORGANISM: Homo sapiens
<220> FEATURE:
<221> NAME/KEY: CDS
<222> LOCATION: (151)..(1341)
<223> OTHER INFORMATION:

<400> SEQUENCE: 1
ggcaggacag gcttagagaa gacgcggtcc ccagcgcttg ggccacggac gtcccacccc         60
gctccttgtc gctggagaac cgccgggccg agccactggg agaagcaggc cagagccttc        120
cagggcctcc ggcccgtgga cccgaggagg atg agc tgg ctt ttt ccc ctg acc        174
                                 Met Ser Trp Leu Phe Pro Leu Thr
                                  1               5 aag agc gcc tcc tcc tcc gcg gct ggg tcc ccc ggt ggc ctc acc agc        222
Lys Ser Ala Ser Ser Ser Ala Ala Gly Ser Pro Gly Gly Leu Thr Ser
        10                  15                  20 ctc cag cag cag aag cag cgc ctg atc gag tcc ctc cgg aac tca cac        270
Leu Gln Gln Gln Lys Gln Arg Leu Ile Glu Ser Leu Arg Asn Ser His
25                  30                  35                  40 tcc agt ata gcc gaa ata cag aaa gat gtg gaa tac aga ttg cca ttc        318
Ser Ser Ile Ala Glu Ile Gln Lys Asp Val Glu Tyr Arg Leu Pro Phe
                45                  50                  55 acc ata aac aac ctg aca att aac att aat ata ttg ctt cct cca cag        366
Thr Ile Asn Asn Leu Thr Ile Asn Ile Asn Ile Leu Leu Pro Pro Gln
            60                  65                  70 ttt cct cag gaa aaa cca gtg atc agt gtt tat cca cca ata cga cat        414
Phe Pro Gln Glu Lys Pro Val Ile Ser Val Tyr Pro Pro Ile Arg His
        75                  80                  85 cac tta atg gat aaa caa gga gtg tat gtt acc tct cca tta gta aac        462
His Leu Met Asp Lys Gln Gly Val Tyr Val Thr Ser Pro Leu Val Asn
    90                  95                  100 aat ttt aca atg cac tca gat ctt gga aaa att att cag agt ctg ttg        510
Asn Phe Thr Met His Ser Asp Leu Gly Lys Ile Ile Gln Ser Leu Leu
105                 110                 115                 120 gat gag ttt tgg aag aat cct cca gtt tta gct cct act tca aca gca        558
Asp Glu Phe Trp Lys Asn Pro Pro Val Leu Ala Pro Thr Ser Thr Ala
                125                 130                 135 ttt cct tat cta tac agt aac cca agt ggg atg tct cct tat gct tct        606
Phe Pro Tyr Leu Tyr Ser Asn Pro Ser Gly Met Ser Pro Tyr Ala Ser
            140                 145                 150
```

| | |
|---|---:|
| cag ggt ttt cca ttt ctt cct cca tat cct cca caa gaa gca aac agg<br>Gln Gly Phe Pro Phe Leu Pro Pro Tyr Pro Pro Gln Glu Ala Asn Arg<br>        155                       160                     165 | 654 |
| agt atc act tct tta tct gtt gct gac act gtt tct tct tca aca aca<br>Ser Ile Thr Ser Leu Ser Val Ala Asp Thr Val Ser Ser Ser Thr Thr<br>    170                     175                    180 | 702 |
| agt cat acc aca gcc aag cct gcc gct cct tca ttt ggt gtc ctt tca<br>Ser His Thr Thr Ala Lys Pro Ala Ala Pro Ser Phe Gly Val Leu Ser<br>185                     190                    195               200 | 750 |
| aat ctg cca tta ccc att ccc aca gtg gat gct tca ata ccg aca agc<br>Asn Leu Pro Leu Pro Ile Pro Thr Val Asp Ala Ser Ile Pro Thr Ser<br>                    205                    210               215 | 798 |
| caa aat ggt ttt ggg tac aag atg cca gat gtc cct gat gca ttt cca<br>Gln Asn Gly Phe Gly Tyr Lys Met Pro Asp Val Pro Asp Ala Phe Pro<br>220                     225                    230 | 846 |
| gaa ctc tca gaa cta agt gtg tca caa ctc aca gat atg aat gaa caa<br>Glu Leu Ser Glu Leu Ser Val Ser Gln Leu Thr Asp Met Asn Glu Gln<br>    235                     240                    245 | 894 |
| gag gag gta tta cta gaa cag ttt ctg act ttg cct caa cta aaa caa<br>Glu Glu Val Leu Leu Glu Gln Phe Leu Thr Leu Pro Gln Leu Lys Gln<br>        250                     255                260 | 942 |
| att att acc gac aaa gat gac tta gta aaa agt att gag gaa cta gca<br>Ile Ile Thr Asp Lys Asp Asp Leu Val Lys Ser Ile Glu Glu Leu Ala<br>265                     270                    275               280 | 990 |
| aga aaa aat ctc ctt ttg gag ccc agc ttg gaa gcc aaa aga caa act<br>Arg Lys Asn Leu Leu Leu Glu Pro Ser Leu Glu Ala Lys Arg Gln Thr<br>             285                    290                  295 | 1038 |
| gtt tta gat aag tat gaa tta ctt aca cag atg aag tcc act ttc gaa<br>Val Leu Asp Lys Tyr Glu Leu Leu Thr Gln Met Lys Ser Thr Phe Glu<br>                 300                    305               310 | 1086 |
| aag aag atg caa agg cag cat gaa ctt agt gag agc tgt agt gca agt<br>Lys Lys Met Gln Arg Gln His Glu Leu Ser Glu Ser Cys Ser Ala Ser<br>           315                    320                 325 | 1134 |
| gcc ctt cag gca aga ttg aaa gta gct gca cat gaa gct gag gaa gaa<br>Ala Leu Gln Ala Arg Leu Lys Val Ala Ala His Glu Ala Glu Glu Glu<br>        330                     335                340 | 1182 |
| tct gat aat att gca gaa gac ttc ttg gag gga aag atg gaa ata gat<br>Ser Asp Asn Ile Ala Glu Asp Phe Leu Glu Gly Lys Met Glu Ile Asp<br>345                     350                    355               360 | 1230 |
| gat ttt ctc agt agc ttc atg gaa aag aga aca att tgc cac tgt aga<br>Asp Phe Leu Ser Ser Phe Met Glu Lys Arg Thr Ile Cys His Cys Arg<br>             365                    370                  375 | 1278 |
| aga gcc aag gaa gag aaa ctt cag cag gcg ata gca atg cac agc caa<br>Arg Ala Lys Glu Glu Lys Leu Gln Gln Ala Ile Ala Met His Ser Gln<br>        380                     385                390 | 1326 |
| ttt cat gct cca cta tagattttcc tggaaacatg aactgccaag agaggaatgg<br>Phe His Ala Pro Leu<br>             395 | 1381 |
| gacacaaaac caaacactgt tttatattta tggtttgcaa actggcattt catcagtggc | 1441 |
| taaattcaca gatatcctat atagattgta tacagaactg agactgattt tgtaccgatt | 1501 |
| agaatgattg ctatgatctt tgagaaattt ttctgcacta tttgcactga aatgtttatt | 1561 |
| tattgttgat aaattgtatc atatttaagt tccactgctg ttcctcttac cttgattaaa | 1621 |
| tgcctatgca tgtacttta gctagttttt aatattttat aaaacttcat ttaaatttgt | 1681 |
| atttttaact tgaagttcca tttctttatc aaggatggta tttagatttt tttcctctta | 1741 |
| accttttttc aaaactatt ttcaactgtg aggaaaccct tatttttctt tctttgtgga | 1801 |
| taaaactttc aaaagcaatt taagatattc atagtgttag gaaacaccaa acctgcctat | 1861 | gtgccatctc acaaaagaaa cttttaatac ctacaataaa tcaaaagaat aaacc        1916

<210> SEQ ID NO 2
<211> LENGTH: 397
<212> TYPE: PRT
<213> ORGANISM: Homo sapiens

<400> SEQUENCE: 2

Met Ser Trp Leu Phe Pro Leu Thr Lys Ser Ala Ser Ser Ala Ala
1               5                   10                  15

Gly Ser Pro Gly Gly Leu Thr Ser Leu Gln Gln Lys Gln Arg Leu
            20                  25                  30

Ile Glu Ser Leu Arg Asn Ser His Ser Ser Ile Ala Glu Ile Gln Lys
                35                  40                  45

Asp Val Glu Tyr Arg Leu Pro Phe Thr Ile Asn Asn Leu Thr Ile Asn
            50                  55                  60

Ile Asn Ile Leu Leu Pro Pro Gln Phe Pro Gln Glu Lys Pro Val Ile
65                  70                  75                  80

Ser Val Tyr Pro Pro Ile Arg His His Leu Met Asp Lys Gln Gly Val
                85                  90                  95

Tyr Val Thr Ser Pro Leu Val Asn Asn Phe Thr Met His Ser Asp Leu
            100                 105                 110

Gly Lys Ile Ile Gln Ser Leu Leu Asp Glu Phe Trp Lys Asn Pro Pro
            115                 120                 125

Val Leu Ala Pro Thr Ser Thr Ala Phe Pro Tyr Leu Tyr Ser Asn Pro
            130                 135                 140

Ser Gly Met Ser Pro Tyr Ala Ser Gln Gly Phe Pro Phe Leu Pro Pro
145                 150                 155                 160

Tyr Pro Pro Gln Glu Ala Asn Arg Ser Ile Thr Ser Leu Ser Val Ala
                165                 170                 175

Asp Thr Val Ser Ser Ser Thr Thr Ser His Thr Thr Ala Lys Pro Ala
            180                 185                 190

Ala Pro Ser Phe Gly Val Leu Ser Asn Leu Pro Leu Pro Ile Pro Thr
            195                 200                 205

Val Asp Ala Ser Ile Pro Thr Ser Gln Asn Gly Phe Gly Tyr Lys Met
210                 215                 220

Pro Asp Val Pro Asp Ala Phe Pro Glu Leu Ser Glu Leu Ser Val Ser
225                 230                 235                 240

Gln Leu Thr Asp Met Asn Glu Gln Glu Val Leu Leu Glu Gln Phe
                245                 250                 255

Leu Thr Leu Pro Gln Leu Lys Gln Ile Ile Thr Asp Lys Asp Asp Leu
            260                 265                 270

Val Lys Ser Ile Glu Glu Leu Ala Arg Lys Asn Leu Leu Leu Glu Pro
            275                 280                 285

Ser Leu Glu Ala Lys Arg Gln Thr Val Leu Asp Lys Tyr Glu Leu Leu
290                 295                 300

Thr Gln Met Lys Ser Thr Phe Glu Lys Lys Met Gln Arg Gln His Glu
305                 310                 315                 320

Leu Ser Glu Ser Cys Ser Ala Ser Ala Leu Gln Ala Arg Leu Lys Val
                325                 330                 335

Ala Ala His Glu Ala Glu Glu Ser Asp Asn Ile Ala Glu Asp Phe
                340                 345                 350

Leu Glu Gly Lys Met Glu Ile Asp Asp Phe Leu Ser Ser Phe Met Glu
            355                 360                 365

Lys Arg Thr Ile Cys His Cys Arg Arg Ala Lys Glu Glu Lys Leu Gln

```
              370                 375                 380
Gln Ala Ile Ala Met His Ser Gln Phe His Ala Pro Leu
385                 390                 395
```

<210> SEQ ID NO 3
<211> LENGTH: 18
<212> TYPE: DNA
<213> ORGANISM: Artificial Sequence
<220> FEATURE:
<221> NAME/KEY: misc_feature
<222> LOCATION: (1)..(18)
<223> OTHER INFORMATION: primer

<400> SEQUENCE: 3
ggcaggacag gcttagag                                        18

<210> SEQ ID NO 4
<211> LENGTH: 22
<212> TYPE: DNA
<213> ORGANISM: Artificial Sequence
<220> FEATURE:
<221> NAME/KEY: misc_feature
<222> LOCATION: (1)..(22)
<223> OTHER INFORMATION: primer

<400> SEQUENCE: 4
ggtttattct tttgatttat tg                                   22

<210> SEQ ID NO 5
<211> LENGTH: 25
<212> TYPE: DNA
<213> ORGANISM: Artificial Sequence
<220> FEATURE:
<221> NAME/KEY: misc_feature
<222> LOCATION: (1)..(25)
<223> OTHER INFORMATION: primer

<400> SEQUENCE: 5
gctctagaat gagctggctt tttcc                                25

<210> SEQ ID NO 6
<211> LENGTH: 23
<212> TYPE: DNA
<213> ORGANISM: Artificial Sequence
<220> FEATURE:
<221> NAME/KEY: misc_feature
<222> LOCATION: (1)..(23)
<223> OTHER INFORMATION: primer

<400> SEQUENCE: 6
cggaattcct ctcttggcag ttc                                  23

<210> SEQ ID NO 7
<211> LENGTH: 26
<212> TYPE: DNA
<213> ORGANISM: Artificial Sequence
<220> FEATURE:
<221> NAME/KEY: misc_feature
<222> LOCATION: (1)..(26)
<223> OTHER INFORMATION: primer

<400> SEQUENCE: 7
ccaagcttga tgagctggct ttttcc                               26

<210> SEQ ID NO 8
<211> LENGTH: 27
<212> TYPE: DNA
<213> ORGANISM: Artificial Sequence

```
<220> FEATURE:
<221> NAME/KEY: misc_feature
<222> LOCATION: (1)..(27)
<223> OTHER INFORMATION: primer

<400> SEQUENCE: 8
cgcgtcgact tcctctcttg gcagttc                                          27
```